United States Patent
Morito et al.

[11] Patent Number: 5,986,752
[45] Date of Patent: Nov. 16, 1999

[54] BORE SCOPE

[75] Inventors: Yuhkoh Morito, Tokyo; Shuichi Nishida, Saitama-Ken, both of Japan

[73] Assignee: Moritex Corporation, Japan

[21] Appl. No.: 08/934,288

[22] Filed: Sep. 19, 1997

[30] Foreign Application Priority Data

Nov. 18, 1996 [JP] Japan ................................. 8-306664

[51] Int. Cl.$^6$ ..................................................... A61B 1/07
[52] U.S. Cl. ........................................ 356/241.5; 600/182
[58] Field of Search ................................. 356/241, 241.1, 356/241.5; 600/182; 385/117

[56] References Cited

U.S. PATENT DOCUMENTS

| | | | |
|---|---|---|---|
| 3,132,646 | 5/1964 | Hett | 600/182 |
| 3,327,712 | 6/1967 | Kaufman et al. | 385/117 |
| 4,281,929 | 8/1981 | Lord et al. | 356/241 |
| 5,369,525 | 11/1994 | Bala et al. | 359/435 |

Primary Examiner—Richard A. Rosenberger
Attorney, Agent, or Firm—Brown, Martin, Haller & McClain, LLP

[57] ABSTRACT

The attempt is to improve the light utilization effect by concentrating and irradiating the light on the observation area, and at the same time, to be able to simply wipe the end clean even when dirtied by oil. Optical fiber light guide 7 for illumination is arranged concentrically on the peripheral part of image incident end part 6 in of image guide 6 that has been inserted inside of pipe 2; that light exit end part 7 out is arranged closer to objective lens 3 than the focal point position of objective lens 3. By doing this, after the light that exits and disperses from light exit end part 7 out has advanced along the optical axis facing the linearly in relation to objective lens 3, the light advances by following along the optical axis which diffracts the light in direction passing through the focal point of the object to be observed side of objective lens 3, and it is possible to irradiate nearly all of the light within the range which can be observed by image guide 6, thus improving the light utilization efficiency. Also, because the end aperture part of pipe 2 in which image guide 6 and image light guide 7 is filled up by the objective lens, the end can be easily wiped clean even when dirtied with oil, etc.

6 Claims, 3 Drawing Sheets

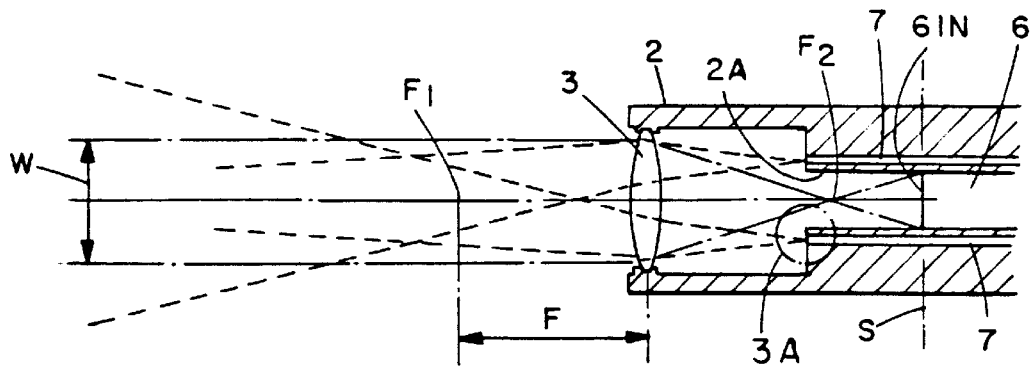
FIG. 3
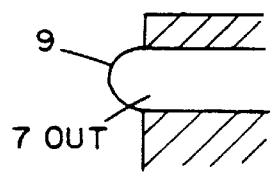
FIG. 3A
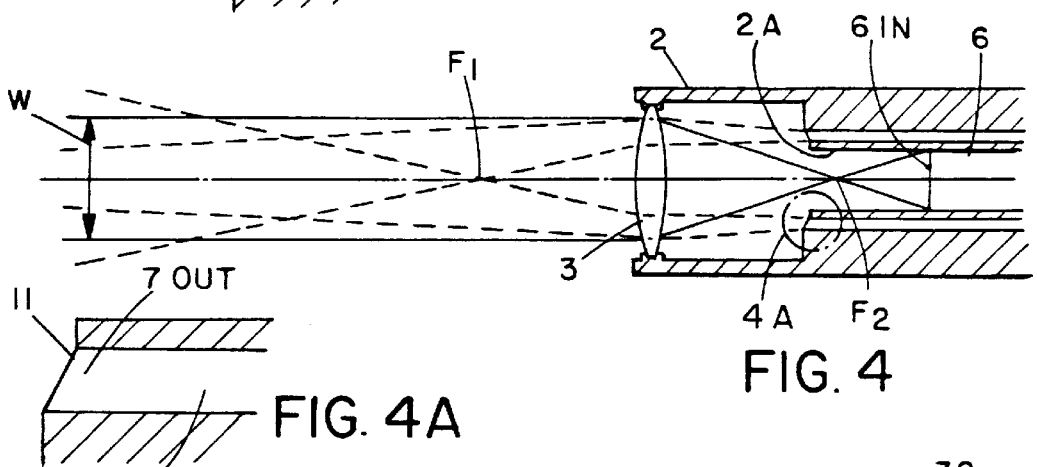
FIG. 4
FIG. 4A
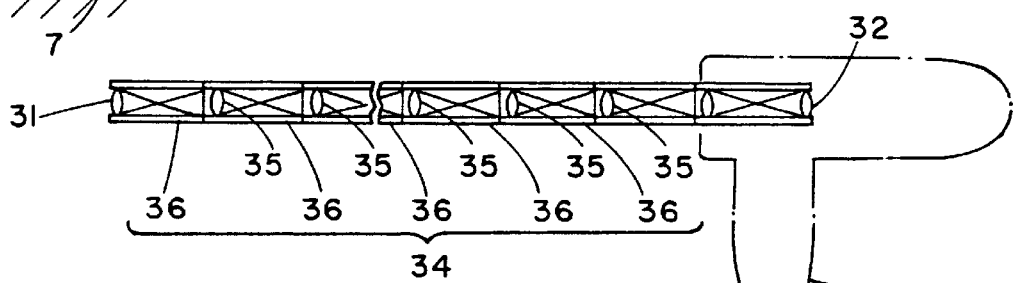
FIG. 6
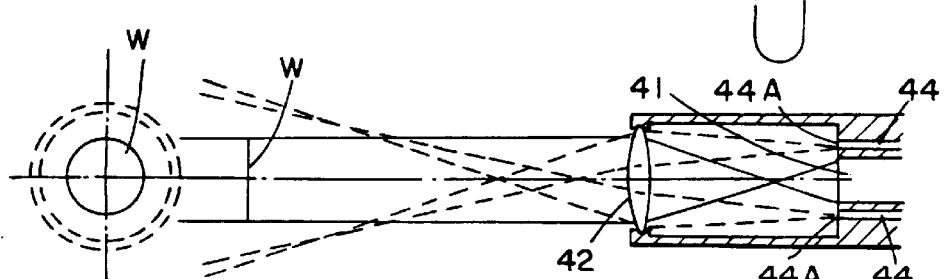
FIG. 8

BORE SCOPE

BACKGROUND OF THE INVENTION

1. Field of the Invention

The present invention is related to a bore scope that is inserted, for example, into the bore hole of an engine cylinder in order to observe the interior without removing the cylinder head.

2. Description of Related Art

When inspecting the interior of engine cylinders at an automobile equipping plant, etc., a bore scope is used to inspect the interior without going to all the trouble to remove the cylinder head.

As indicated in FIG. 6, objective lens 31 is arranged on one end, and lenses 35 are arranged coaxially in a series at specified distances within rigid barrel 34, on the other end of which is mounted eyepiece 33 that provides ocular lens 32.

Then, when this objective lens 31 side of barrel 34 is brought near the observation area, the light image, which is incident through objective lens 31, can be observed on the eyepiece 33 side.

However, because this linked lens system arranges multiple lenses 31, 32, 35, 35 coaxially in a series, it is difficult to bring out light axis precision, and there is the problem that a clear image cannot be obtained if there is the slightest light axis discrepancy.

Also, when attempting to illuminate the object to be observed, there is the problem that, because rehalation occurs in which light is randomly reflected within barrel 33 when the illumination light passes through the inside of the barrel and is made incident upon the object to be observed, a separate light bulb must be provided, for example, on the end peripheral surface of barrel 33 so that the object to be observed can be illuminated from the outside of the barrel, and thus the end becomes large scale.

Furthermore, there is also the conventional example in FIG. 7. Objective lens 42 is arranged on the end of image guide 41 which consists of bundled fibers, and fiberscope 40, on which is mounted eyepiece 45 that provides ocular lens 43 on the other side of image guide 41, does not have light axis discrepancies because objective lens 42 and ocular lens 43 are arranged on the two ends of image guide 41. Moreover, because the light exit end 44a of light guide 44 is arranged in a ring-shape on the periphery of objective lens 42, when this is applied to the bore scope, the illumination light can illuminate the object to be observed without making the end large scale.

Nonetheless, there is the problem that, because the light which exits from ring-shaped light exit end part 44a of light guide 44 is dispersed to outside the range which image guide 41 can observe, the light utilization efficiency is poor, with the amount of light incident on the object to be observed being a scant 20–30% of the total amount of light exiting from light guide 44.

Also, light exit end part 44a of light guide 44 is arranged on the periphery of objective lens 42 and is exposed at the end surface, and if the end of image scope 40 becomes dirty with oil, etc. when, for example, observing the interior of an engine cylinder, the oil adhering to the lens surface of objective lens 42 can be wiped off relatively easily because that surface is smoothly curved, but because the light exit end part 44a of light guide 44 is arranged on the periphery of objective lens 44 in a ring-shape that exposes the ends of multiple optical fibers, the oil adhering to light exit end part 44a can not be wiped off cleanly, and consequently, there is the problem that there is great light loss.

Of course, if light exit end part 44a of light guide 44 is arranged inside of objective lens 42, there is no such problem because light exit end part 44a is protected by objective lens 42, but in that case, as indicated in FIG. 8, the illumination light is incident in a ringshape that surrounds the outside of observation range W, and it is not possible to illuminate the object to be observed efficiently at the area to be brought into focus.

Thus, the present invention improves the light utilization efficiency by making the light fall in a manner concentrated on the area to be observed, and, at the same time, addresses the technical issue of making it easy to wipe off the tip even when it is dirtied by oil, etc.

SUMMARY OF THE INVENTION

In order to solve these problems, the present invention involves a bore scope in which an objective lens is arranged on the end of a linearly formed pipe and an eyepiece provided with an ocular lens is mounted on the other end so that light images incident from the objective lens side are observed with the eyepiece by bringing the end of aforementioned pipe close to the observation area; and is characterized: by the end aperture part of the aforementioned pipe being filled up by the aforementioned objective lens; by a light exit end of an illumination optical fiber light guide being inserted therein concentrically on the periphery of an image incident end part of an image guide with the aforementioned image incident end part being arranged on the image focal plane set in advance to correspond to the focal distance of the objective lens; and by the aforementioned light guide being arranged such that the distance from that light exit end part up to the objective lens is shorter than the focal distance of the objective lens.

According to the present invention, because the image incident end part of the image guide that is inserted inside the pipe is arranged on the previously set focal plane of the objective lens, the image of the object to be observed, which is at a position separated from the objective lens at just the specified distance, is formed on the image incident end part, is transferred within the image guide, and is enlarged by the objective lens arranged on the other end.

Moreover, the optical fiber guide for illumination is arranged in a concentric circular shape on the periphery of that image incident end part, and because that light exit end part is arranged nearer to the objective lens than the focal point position of the objective lens, after the light that is dispersed from and exits that light exit end part advances along the light axis, which faces in a linear direction to the objective lens, nearly all of that light can be incident within the range that can be observed by the image guide, thus improving the light utilization efficiency.

At this time, because the pipe and aperture part in which the image guide and light guide are inserted is filled up by the objective lens, the end surface can be easily wiped off even when dirtied by oil adhering to the tip, and no dirt remains on the light exit end part of the light guide.

BRIEF DESCRIPTION OF THE DRAWINGS

The present invention will be better understood from the following detailed description of a preferred embodiment of the invention, taken in conjunction with the accompanying drawings, in which like reference numerals refer to like parts, and in which:

FIG. 2E is an enlargement of the portion circled and labeled 2E in FIG. 2C;

FIG. 3 is a light line diagram of the objective lens system;

FIG. 4 is a light line diagram indicating another embodiment;

FIG. 6 is a diagram indicating the linked lenses of a conventional bore scope;

FIG. 8 is a light line diagram of the light guide arranged inside the objective lens.

DESCRIPTION OF THE PREFERRED EMBODIMENTS

Figure 1:
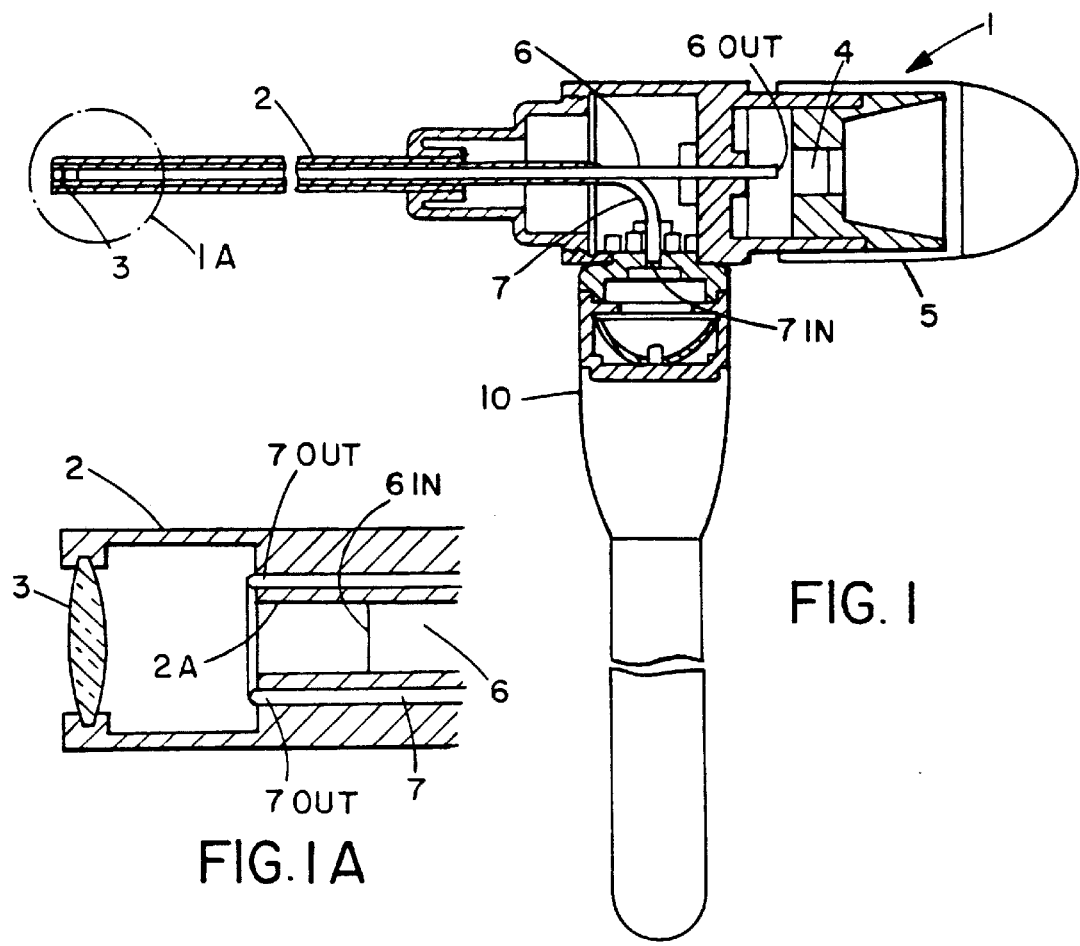
FIG. 1 is a cross-sectional diagram indicating one example of a bore scope related to the present invention.
Figure 1A:
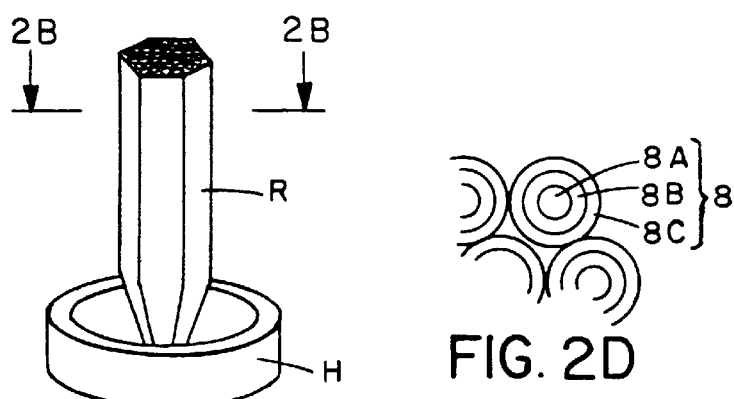

Below, embodiments of the present invention will be specifically explained based on the diagrams.

Bore scope 1 of this example has objective lens 3 arranged so that it fills up the end aperture part of highly rigid, protective pipe 2 that is formed linearly, and eyepiece 5 that provides ocular lens 4 is formed on the rear end. Multi-core structure image conduit (image guide) 6, in which image incident end part 6 in and image exit end part 6 out are facing aforementioned objective lens 3 and ocular lens 4 respectively, is inserted within aforementioned protective pipe 2. Optical fiber light guide 7 for illumination, which illuminates the object to be observed through aforementioned objective lens 3, is inserted such that light exit end part 7 is arranged in a cylindrical shape around image incident end part 6 in of image conduit 6.

Also, light shade pipe 2a to prevent mutual leakage of light is mounted between aforementioned image conduit 6 and optical fiber light guide 7 for illumination, which is added to this.

Figure 2D:
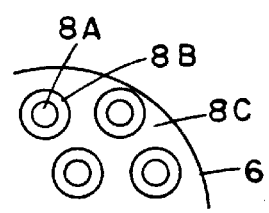
FIG. 2D is an enlargement of the portion circled and labeled 2D in FIG. 2B.
Figure 2A:
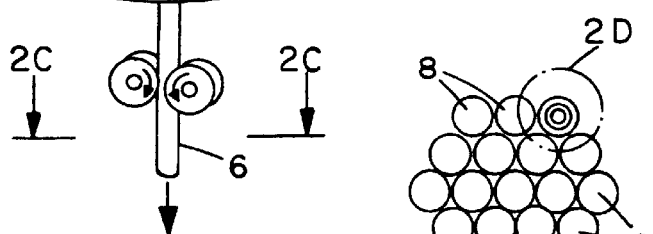
FIG. 2A indicates the manufacturing method of the image conduit.
Figure 2B:
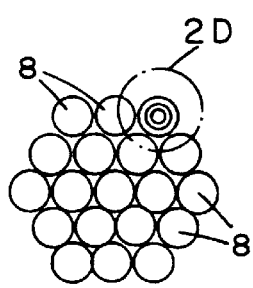
FIG. 2B is the cross-section of the 2B—2B line of FIG. 2A.
Figure 2C:
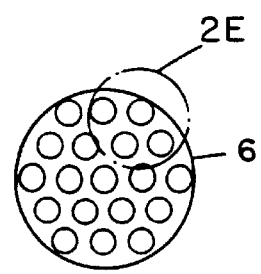
FIG. 2C is the cross-section of the 2C—2C line of FIG. 2A.
Figure 5A:
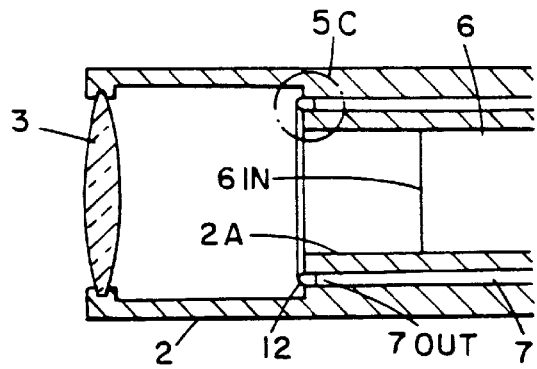
FIGS. 5A and B are diagrams indicating the essential parts of another embodiment.
Figure 5C:
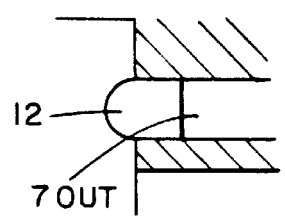
FIGS. 5C and 5D are enlargements of the circled portions labeled 5C and 5D in FIGS. 5A and 5B, respectively.
Figure 5B:
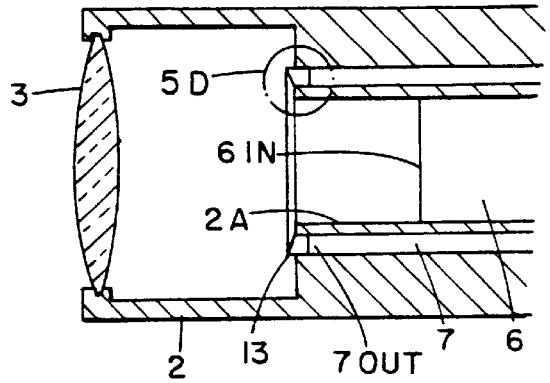
Figure 5D:
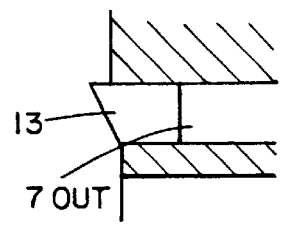
Figure 7A:
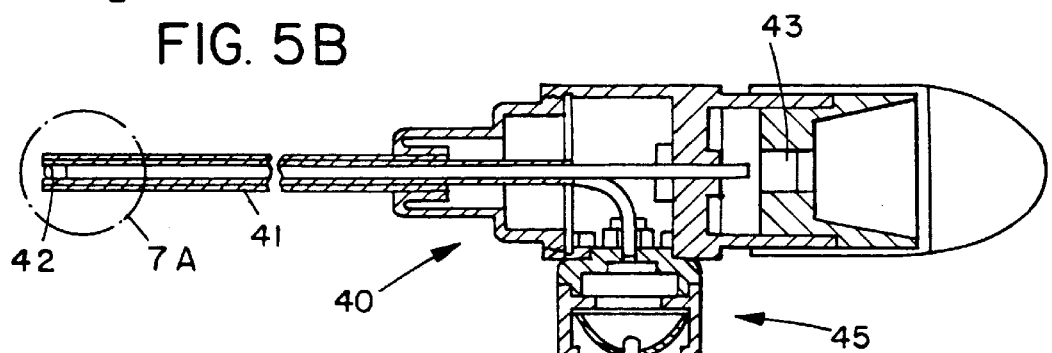
FIGS. 7 and 7A are diagrams indicating a conventional bore scope.
Figure 7A:
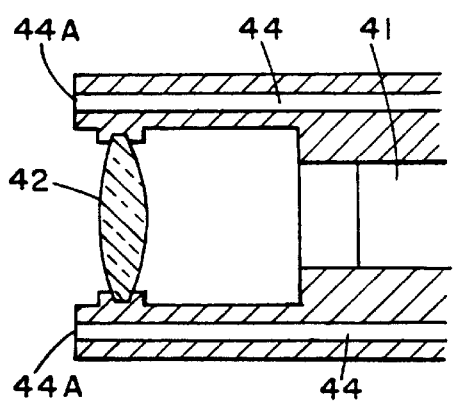
Figure 7:
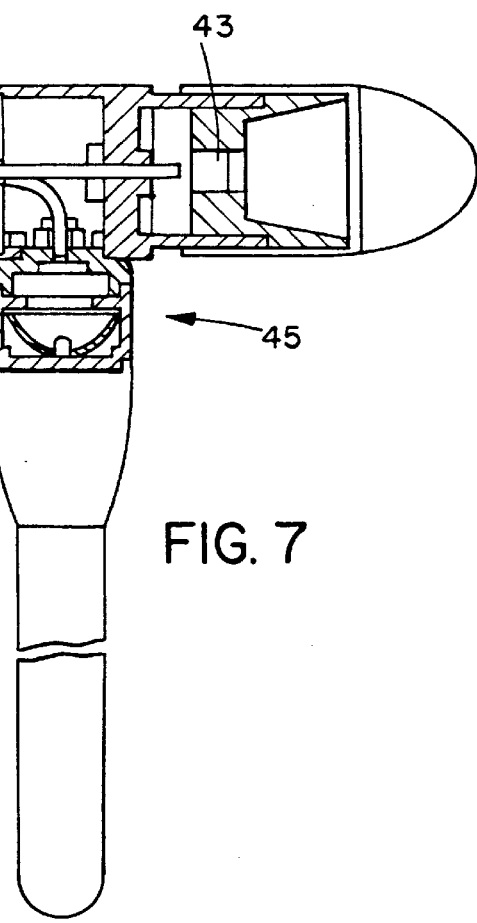

FIG. 2A indicates the manufacturing method of image conduit 6, FIG. 2B is the cross-section of the 2B—2B line, and FIG. 2C is the cross-section of the 2C—2C line while FIG. 2D is an enlargement of the circled area labeled 2D in FIG. 2B and FIG. 2E is an enlargement of the circled area labeled 2E in FIG. 2C. Element rod R is formed in advance into a yarn by bundling together 3-layer structure element fibers 8, which are formed by core 8A in the center, clad 8B in the middle and fusion glass 8C on the outside, and then by heating with heater H. Image conduit 6 is thus formed into the specified shape and dimensions by mutually fusing together fusion glass layers 8C of element fibers 8.

Then, aforementioned image incidental end part 6 in of image conduit 6 is arranged on the focal plane S which is set in advance to correspond to focal distance f of aforementioned objective lens 3; optical fiber light guide 7 for illumination is arranged by positioning light exit end part 7 out closer to the objective lens 3 side than ocular side focal point F2 of objective lens 3 such that the distance from light exit end part 7 out to objective lens 3 is shorter than focal point distance f of objective lens 3. By doing this, that exit light advances along the optical axis and is diffracted in the direction passing though object side focal point F1 of objective lens 3 so as to centrally illuminate observation range W. Also, light exit end part 7 out of optical fiber guide 7 for illumination is formed into spherical boundary surface 9, and, by that effect, narrows the light diffusion angle by which light exits from said light exit end part 7 out.

Furthermore, 10 is the light source device by which light is made incident on light incident end 7 in of optical fiber light guide 7 for illumination, and is formed into a single piece with the aforementioned eyepiece 5.

The above is an example of a configuration of the present invention, and next, the action of this will be explained.

For example, if f is the focal distance of objective lens 3 and 1.5 f is the distance between objective lens 3 and focal plane S, focus would be achieved at a distance separated 3f from the objective lens.

At this time, light exit end part 7 out of optical fiber guide 7 for illumination is formed into spherical diffraction surface 8, and therefore the dispersion angle of the light that exits from the light exit end part 7 out becomes smaller. Also, because the distance from light exit end part 7 out to objective lens 3 is set to be shorter than focal distance f of objective lens 3, the light passing through objective lens 3 does not cohere into a ring-shape.

Then if, for example, the distance up to objective lens 3 is set to f×⅚, that exit light is diffracted in the direction passing though the object side focal point F1 of objective lens 3, as indicated by the broken line in FIG. 2, and advances along the optical axis. Because nearly all of this centers on observation range W and is incident on observation range W, the light utilization efficiency is extremely high, and it is possible to have brighter illumination using a light source with the same amount of light.

When inserting this kind of bore scope through a plug mount hole of an engine and observing inside the cylinder, because the image comes into focus when objective lens 3 approaches a distance 3f to the inner surface of the cylinder and the light exiting from optical fiber light guide 7 for illumination centrally illuminates the part that can be observed by image conduit 6, that image of the inner surface of the cylinder is enlarged by ocular lens 4 and can be observed.

At this time, light shade pipe 2a is mounted on the exterior of image conduit 6, and because optical fiber light guide 7 for illumination is added around it, there is no reduction of the surface image quality caused by the light transmitted through said light guide 7 leaking to the image conduit 6 side.

Also, even if oil, etc. adheres to the tip of protective pipe 2 when the bore scope is inserted in the cylinder, because the end aperture part of protective pipe 2 is filled up with objective lens 3, no oil, etc. will adhere to the light incident end part 6 in of image conduit 6 or to light exit end part of optical fiber light guide 7 for illumination, and dirt can be removed relatively easily just by wiping off the oil that adheres to objective lens 3.

Furthermore, light exit end part 7 out of optical 20 fiber light guide 7 for illumination is not limited to being formed into spherical boundary surface 8, and a slanted boundary surface 11 may also be formed, as indicated in FIG. 4.

In this case, after the light which exits from light exit end part 7 out is diffracted by aforementioned boundary surface 11 and faces the outside from said exit end part 7 out, it is further diffracted by objective lens 3 and illuminates observation range W, and therefore the part which illuminates the periphery of observation range W becomes smaller and can further improve the light utilization efficiency.

Also, as indicated in FIGS. 5A to 5D, ring-shaped lens 12 and 13 may be arranged between light exit end part 7 out and objective lens 3.

Of course, the position of light exit end part 7 is selected such that it can effectively illuminate observation range W that is focused corresponding to focal plane S. In order to more effectively illuminate observation range W with light, light exit end part 7 out may be formed on boundary surfaces 9 and 11 with ring-shaped lenses 12 and 13 arranged between light exit end part 7 and objective lens 3. If it achieves that purpose, the shape of the boundary surface formed on light exit end part 7 out and the aforementioned ring-shaped lens may be optionally adopted.

As described above, according to the present invention, because the light exit end part of the optical fiber light guide for illumination is concentrically arranged on the periphery of the image incident end part of the image guide, and also because the distance between said light exit end part and the objective lens is shorter than the focal distance, after the light which exits and is dispersed from that light exit end part has directly advanced toward the objective lens, the light advances along the optical axis which diffracts the light in a direction to pass through the focal point on the object to be observed of the objective lens, and nearly all of that light illuminates within the range that can be observed by the image guide. Thus, the light utilization efficiency is improved. Furthermore, because the end aperture part of the pipe, through which the image guide and light guide are inserted, is filled up with the objective lens, and this has the greatly superior effect that the device can be easily wiped clean even when dirtied by oil, etc. adhering to that end surface, and no dirt remains on the light exit end part of the light guide.

Although a preferred embodiment of the invention has been described above by way of example only, it will be understood by those skilled in the field that modifications may be made to the disclosed embodiment without departing from the scope of the invention, which is defined by the appended claims.

We claim:

1. A bore scope, comprising:

an elongate pipe having opposite first and second ends, the first end forming an aperture of predetermined diameter;

an objective lens mounted in the first end of the pipe, the objective lens having a diameter substantially equal to that of the aperture at the first end of the pipe, whereby the objective lens fills the aperture, and the objective lens having a predetermined focal length;

an eyepiece provided with an ocular lens mounted on the second end of the pipe, whereby light images incident from the objective lens are observed with the eyepiece by bringing the first end of the tube close to an observation area;

a ring-shaped illumination optical fiber light guide extending concentrically along the pipe and having a light exit end spaced inwardly from the objective lens by a first distance less than the focal length of the objective lens; and an image guide arranged within the pipe to extend concentrically within the optical fiber light guide, the image guide having an image incident end spaced inwardly from the objective lens at an image focal plane of the objective lens;

the objective lens comprising means for forming an image of an object to be observed at the image incident end of the image guide.

2. The bore scope as claimed in claim 1, wherein the image guide comprises a bundle of optical fibers each having a three layer structure of a central core, a middle cladding layer, and an outer fusion glass layer, the outer fusion glass layers of the fibers being fused together.

3. The bore scope as claimed in claim 1, wherein the light exit end of the optical fiber light guide is formed into a spherical shape, whereby diffraction is caused such that light exiting from said light exit end is incident upon the observation area.

4. The bore scope as claimed in claim 1, wherein the light exit end of the optical fiber light guide is formed into a slanted shape, whereby diffraction is caused such that light exiting from said light exit end is incident upon the observation area.

5. The bore scope as claimed in claim 1, including a ring shaped lens positioned between the light exit end of the optical fiber light guide and the objective lens, the ring shaped lens comprising means for causing diffraction whereby light exiting from said light exit end is incident upon the observation area.

6. The bore scope as claimed in claim 1, including a light shading tube mounted on the outside of the image guide between the image guide and optical fiber light guide, the light shading tube extending along the length of the image guide to prevent leakage therefrom.

* * * * *